United States Patent [19]

Darling

[11] Patent Number: 5,076,289
[45] Date of Patent: Dec. 31, 1991

[54] INTRAVENOUS SUPPORT MEANS

[76] Inventor: Harold E. Darling, 5129 N. 15th St., #138, Phoenix, Ariz. 85014

[21] Appl. No.: 619,192

[22] Filed: Nov. 28, 1990

[51] Int. Cl.⁵ .................................................. A61F 5/37
[52] U.S. Cl. ..................... 128/877; 128/878; 128/879; 128/DIG. 6; 128/DIG. 15
[58] Field of Search .................... 128/878, DIG. 6, 77, 128/87 A, 89 R, 879, DIG. 15, 165, 877; 273/54 R, 54 B; 2/16, 20, 161 A, 164

[56] References Cited

U.S. PATENT DOCUMENTS

| D. 259,955 | 7/1981 | Helferich | 128/77 |
|---|---|---|---|
| 2,369,115 | 2/1945 | Bloom | 128/165 |
| 2,369,210 | 2/1945 | Capossela | 273/54 B |
| 2,924,458 | 2/1960 | Barry | 273/54 B |
| 3,238,939 | 3/1966 | Stubbs | 128/165 |
| 3,333,850 | 8/1967 | Miller | 273/54 B |
| 3,369,258 | 2/1968 | Smith | 273/54 B |
| 3,512,776 | 5/1970 | Thomas | 128/165 |
| 3,533,407 | 10/1970 | Smith | 128/165 |
| 3,704,994 | 12/1972 | Krzewinski | 273/54 B |
| 4,198,709 | 4/1980 | Clayton | 273/54 B |
| 4,915,097 | 4/1990 | West | 128/77 |
| 4,982,744 | 1/1991 | Stanec | 128/879 |

Primary Examiner—Robert A. Hafer
Assistant Examiner—Michael Brown
Attorney, Agent, or Firm—Richard R. Mybeck

[57] ABSTRACT

A device for securing and restraining an intravenous line while the line is inserted into the arm of a patient including a fabric wrap anchorable by the patient's thumb and circumscribable about the patient's hand for detachable attachment to itself while sandwiching a loop of the intravenous line therebetween. A slit is provided to pass the intravenous loop through the wrap for engagement by the thumb.

15 Claims, 1 Drawing Sheet

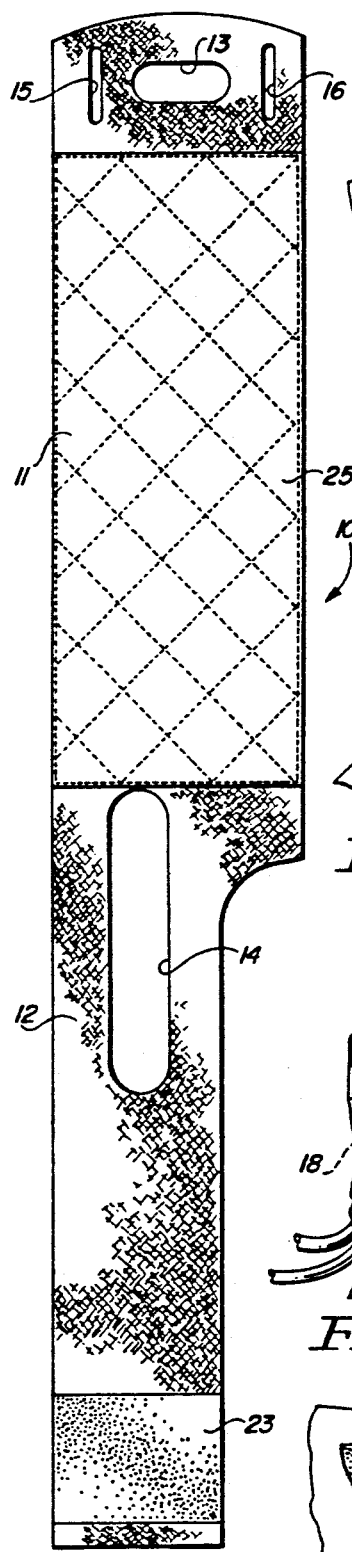
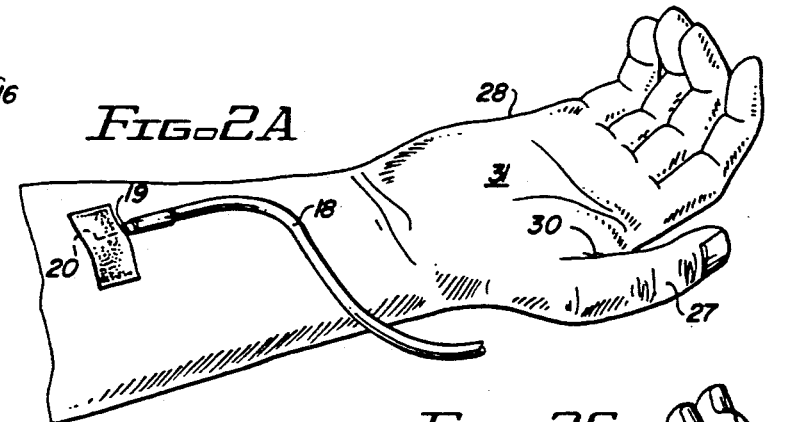
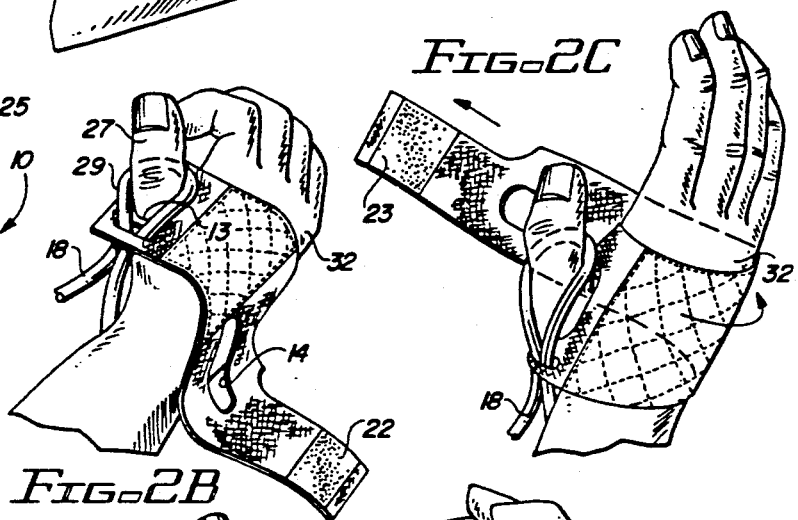
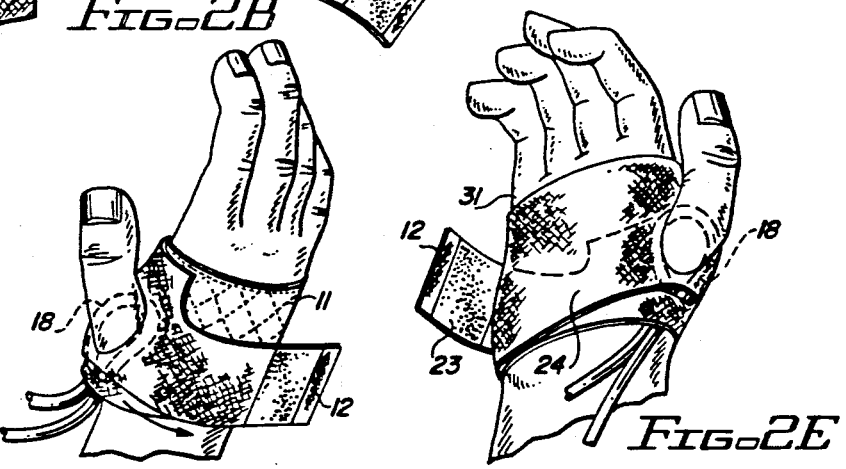
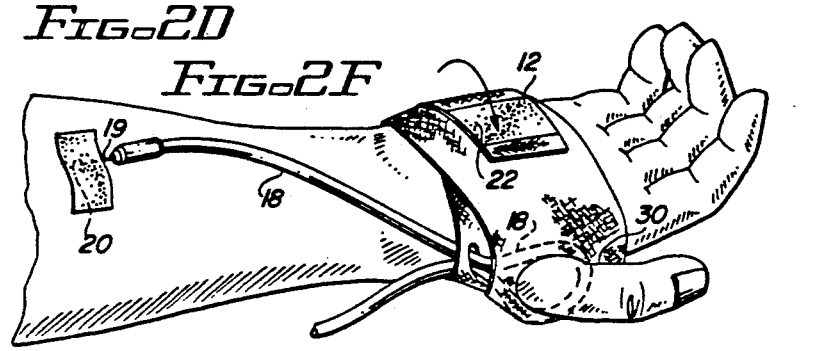

INTRAVENOUS SUPPORT MEANS

INTRODUCTION

The present invention relates to a medical accessory and more particularly to a new and unique non-adhesive means for supporting the attachment of an IV line to a patient.

BACKGROUND OF THE INVENTION

The intravenous (IV) administration of fluids to patients is often a medical necessity. Many diverse and varied fluids are commonly administered in this manner.

Customarily, a needle is used to insert a catheter into a vein in the patient's arm or other body location. After the catheter is firmly inserted in the vein, it is secured to the patient as with a small strip of adhesive tape. The IV line is then started as quickly as possible that is, within a minute or two, to avoid clotting.

Inserting a catheter into a vein is not painless. More importantly, both the fluids themselves and those which contain other therapeutic agents often must be administered at precise rates. An unplanned cessation of therapy such as results from the line becoming unstuck can therefore range from an annoyance to a serious problem. Further, the ability of the patient to use the hand or arm so connected to an IV line is greatly reduced. Accordingly, firmly securing the IV line to the patient is important. To date, no wholly satisfactory means has been found to secure the line without risk of detachment arising from patient movement.

The only solution that has been found heretofore involves the applying layers of adhesive tape, to secure the catheter to the arm of the patient, one remote from and one at the IV site. This has been less than satisfactory both because of the propensity of the adhesive to become detached as well as the irritation caused by the adhesive in many patients, particularly those having unduly hairy arms or heightened sensitivity to adhesive.

Thus a need exists to provide a means to support an IV line which is installed to provide vital fluid to a patient. Such means must secure the line firmly at the administration site and at the same time minimize the use of adhesive tape and like irritants in securing the line while allowing the patient the ability to better use the hand or arm so connected without fear of detaching the line therefrom. It is toward the solution of this problem that the present invention is directed.

BRIEF SUMMARY OF INVENTION

The present invention relates to an intravenous support means which combines the coaction of specially prepared wrap which surrounds a patient's hand, and the hand itself to secure an IV line inserted into a vein in the patient's lower arm. The wrap includes an opening for the patient's thumb, and two slits adjacent thereto, to allow the wrap to be used in either a left handed or right handed configuration. The wrap is secured in place by any convenient fastening device which is easily secured and released intentionally, but which is difficult to release unintentionally.

The IV line is looped around the patient's thumb after passing through one of the slits in proximity thereto, intermediate its source and the insertion site into the patient's vein in the lower portion of the arm with which the wrap is worn. Regardless of arm motion, the distance between the IV site and the patient's thumb remain constant. The line is secured thereabout. Accordingly, movement of the hand and arm induce no dimensional change in the secured portion of the line and no concomitant stress which would otherwise cause the needle and/or the line to become disengaged.

Accordingly, it is a prime object of the present invention to provide a new and improved support means for non-adhesively securing a IV catheter to a patient including a wrap-a-round thumb lock support for securing the feeder line so that the line and the needle are maintained in a relatively stationery position relative to the patient once the needle is installed.

An additional object of the present invention is to provide support means for IV lines and the like which enhance the freedom of movement and manual capacity for patients attached to such IV lines.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

BRIEF DESCRIPTION OF THE DRAWINGS

In the drawings:

FIG. 1 is a plan view of a support means for intravenous tubing in accordance with the present invention;

FIG. 2A is an isometric view of a patient's arm having an IV tube and needle inserted therein;

FIG. 2B is an isometric view of a patient's hand at the first step of installing the support means of FIG. 1;

FIG. 2C is an isometric view of a second step in installing the support means of FIG. 1;

FIG. 2D is an isometric view of a third step in installing the support means of FIG. 1 from the rear of the patient's hand;

FIG. 2E is an isometric view of the third step shown in FIG. 2D from the palm of the patient's hand; and FIG. 2F is an isometric view of the patient's hand and forearm with the support means and IV line and needle fully installed.

DESCRIPTION OF PREFERRED EMBODIMENTS

The support means of the present invention is identified throughout by the general reference numeral 10. Each support means 10 comprises an integral fabric wrap or body portion 11 and an overwrapping portion 12 which is integrally formed with body portion 11 and extends axially therefrom. A first and second thumb aperture 13, 14 is cut through body portion to secure support means 10 in a manner to be hereinafter described in detail. First and second slits 15, 16 are disposed in spaced generally parallel relationship to each other and in spaced relationship to elongated thumb aperture 13 as shown in FIG. 1. As will appear, slits 15, 16 allow insertion of a portion of an IV fluid line 18 therethrough to provide, when line 18 has been attached to the patient's lower arm as with a needle 19 at insertion site 20, a "strain relief" arrangement for line 18 in coaction with the patient's hand when support means 10 is installed as will be hereinafter described in greater detail.

Suitable securing means 22, such as Velcro® "hooks" 23 and Velcro® "loops" 24, allow means 10 to be securely and adjustably fitted to the hand of the patient. An optional foam pad 25 may be attached to the inner surface of body portion 11 to enhance the wearability and comfort of support means 10 and to absorb any leakage occurring from the insertion site 20. Note that in current medical practice, an IV line is normally in place for a period of about three days before replacement occurs.

In practice, support means 10 can be fitted to either hand of the patient in the following manner. Thumb 27 of the patient's hand 28 is inserted through first thumb hole 13. Intravenous fluid line 18 is looped and the loop 29 is passed through one of slits 15, 16, depending upon which hand of the patient is to be wrapped.

Thus, if it is the right hand to be wrapped, thumb 27 is inserted into and through thumb hole 13 and support means 10 is wrapped across the back of hand 28 so that slit 16 is "proximal" to insertion site 20 and slit 15 is distal to insertion site 20. Therefor, for a right hand installation, loop 29 will be passed through slit 16, the proximal slot, and slit 15 will not be used.

For the left hand, thumb 27 is again inserted into and through thumb hole 13 and support means 10 is wrapped across the back of the hand 28 so that slit 15 is "proximal" to insertion site 20 and slit 16 is "distal" to insertion site 20. Thus, for a left hand installation, loop 29 will be passed through slit 15, the proximal slot, and slit 16 will not be used.

Once the support means 10 is anchored to the patient's appropriate thumb 27, that is, the thumb occurring on the same arm as does insertion site 20 and loop 29 is passed through the proximal slit 15, 16 as described above, the loop 29 is passed around the patients thumb 27 and slid into crotch 30 between thumb 27 and the patient's palm 31 and adjusted to provide a loose drape without allowing any unnecessary slack or kink potential in line 18 between insertion site 20 and thumb 27.

The wrapping of support means 10 about the patient's hand 28 now commences. Body portion 11, with foam pad 25, if used, is drawn across the back 32 of hand 28 and over thumb 27 which is inserted through thumb aperture 14 to cover loop portion 29 which in effect is "sandwiched" between body portion 11 and wrap portion 12. Overwrap portion 12 is then passed across back 32 of hand 28, as shown in FIG. 2D, and secured by securing means 22 to restrain IV line. Overwrap portion 12 is engaged to the outer surface of body portion 11 by suitable means such as by the coaction of Velcro® hooks 23 and Velcro® loops 24. Removal of support means 10 is readily effected by separating the Velcro® components 23, 24 and by gradually and continually unwinding means 10 from about the hand 28 while loop 29 in IV line 18 is removed from about thumb 27 and out of the corresponding slit 15, 16.

The "strain relief" feature of device 10 provides increased mobility for the patient who is receiving IV therapy from that obtained using prior approach of taping the IV line to the patient's hand. Furthermore, the patient so taped must, of necessity, use his hand as little as possible so as to reduce the strain applied to IV line, and in particular to the catheter to avoid unwanted and potential dangerous detachment from the insertion site 20. For a patient who is ambulatory and has full use of his other hand, this is a major inconvenience.

Support means 10, on the other hand, permits a patient who must use the hand 28 to which line 18 is attached in order to be mobile, allows the patient to use hand 28 when confined to hand powered wheelchairs, crutches, mobile IV stands or the like, thereby maintaining self-reliance and personal mobility. No substantial stress is placed on that portion of IV line 18 intermediate the insertion site 20 and the thumb 27, because loop 29 is essentially isolated from the balance of line 18.

Any stress induced on line 18 by the movement of hand 28 is mitigated and absorbed by the action of loop 29 and thumb 27 with means 10 to maintain a constant separation. As a consequence of passing through proximal slit 15, 16 and looped around thumb 27, that portion of line 18 intermediate thumb 27 and insertion site 20 is isolated from stress and no torsional or transverse forces can be applied to the isolated portion of line 18 and transmitted to site 20, these forces could otherwise cause discomfort to the patient or worse, cause needle 19 to be pulled out of site 20.

Other conventional securing means 22 can be employed to secure means 10 to patient's hand 28 so long as it does not engage the patient's skin. Velcro® fasteners are simple, easy, and renewable.

In looping line 18 about thumb 27 any stress induced in line 18 by the movement of hand 28 is absorbed by thumb 27 and/or that portion of line 18 which lies intermediate proximal slit 15, 16 and the site 20.

Slits 15, 16 are provided so that support means 10 is ambidextrous. Only one slit 15, 16 is used, the one designated "proximal" depending upon the hand on which the invention is worn. If desired, means 10 can be fabricated in right handed and left handed models in which case only the proximal slit 15 would be required.

While fabric is the preferred material for the construction of means 10, other soft materials can be used for certain embodiments. Further, thumb aperture 14, in such embodiments, can be a simple cut or slit through the wrap portion 12 so long as it extends longitudinally a sufficient length to accommodate hands of different girth.

From the foregoing, it is readily apparent that a new and improved IV support means and accessories therefor has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. A device for securing an intravenous line to the arm of a patient, said arm having a hand with a thumb depending therefrom and containing a vein therein into which said intravenous line is inserted, said device comprising; a fabric member circumscribable around the hand of such patient and detachably securable to itself, said member having a first aperture and a second aperture defined therein in spaced relationship to each other for receiving the thumb of said hand therewithin in the course of circumscribing said hand with said member and a proximal slit in spaced adjacent relationship to said first aperture for receiving a loop of said line therethrough for looped engagement around said thumb.

2. A device according to claim 1 wherein said slit, said member, and said line interact with the patient's hand to effectively eliminate forces which could detach said line from said vein when said hand is moved.

3. Support means for securing an IV line with a human hand having a thumb comprising: a body portion having a distal and a proximal end portion; a wrap portion integrally formed with said proximal end portion of said body portion and extending axially therefrom to a remote end; a first thumb aperture defined in said body portion adjacent said distal end portion thereof; a second thumb aperture defined in said wrap portion adjacent said proximal end portion of said body portion; a slit member defined in said body portion adjacent said first thumb aperture in spaced relationship thereto; and detachable securing means affixed to said wrap portion adjacent said remote end and actuatable to secure said wrap portion to said body portion when said body portion and said wrap portion are disposed in circumscription about said human hand and said IV line is passed through said slit member for looped engagement about said thumb.

4. A support means according to claim 3 in which said first thumb aperture extends transversely of said body portion.

5. A support means according to claim 4 in which said second thumb aperture extends axially of said wrap portion.

6. A support means according to claim 5 in which said body portion has an absorbent pad secured thereto in intimate surface engagement therewith.

7. A support means according to clam 6 in which said detachable securing means comprises coactive hooks and loops.

8. A support means according to claim 5 in which said detachable securing means comprises coactive hooks and loops.

9. A support means according to claim 4 in which said body portion has an absorbent pad secured thereto in intimate surface engagement therewith.

10. A support means according to claim 4 in which said detachable securing means comprises coactive hooks and loops.

11. A support means according to claim 3 in which said second thumb aperture extends axially of said wrap portion.

12. A support means according to claim 11 in which said body portion has an absorbent pad secured thereto in intimate surface engagement therewith.

13. A support means according to claim 3 in which said body portion has an absorbent pad secured thereto in intimate surface engagement therewith.

14. A support means according to claim 13 in which said detachable securing means comprises coactive hooks and loops.

15. A support means according to claim 3 in which said detachable securing means comprises coactive hooks and loops.

* * * * *